US009649256B2

(12) United States Patent
Markl et al.

(10) Patent No.: US 9,649,256 B2
(45) Date of Patent: May 16, 2017

(54) DEVICE AND METHOD FOR MONITORING A PROPERTY OF A COATING OF A SOLID DOSAGE FORM DURING A COATING OF THE SOLID DOSAGE FORM

(71) Applicants: Research Center Pharmaceutical Engineering GmbH, Graz (AT); Research Center for Non Destructive Testing GmbH, Linz (AT)

(72) Inventors: Daniel Markl, Graz (AT); Guenther Hannesschlaeger, Linz (AT); Michael Leitner, Linz (AT); Stephan Sacher, Graz (AT); Daniel Koller, Graz (AT); Johannes Khinast, Graz (AT)

(73) Assignees: Research Center Pharmaceutical Engineering GmbH, Graz (AT); Research Center for Non Destructive Testing GmbH, Linz (AT)

( * ) Notice: Subject to any disclaimer, the term of this patent is extended or adjusted under 35 U.S.C. 154(b) by 115 days.

(21) Appl. No.: 14/265,328

(22) Filed: Apr. 29, 2014

(65) Prior Publication Data

US 2014/0322429 A1 Oct. 30, 2014

(30) Foreign Application Priority Data

Apr. 30, 2013 (GB) .................................. 1307734.2

(51) Int. Cl.
*A61J 3/00* (2006.01)
*G01N 21/84* (2006.01)
(Continued)

(52) U.S. Cl.
CPC .......... *A61J 3/005* (2013.01); *G01B 9/02091* (2013.01); *G01B 11/0625* (2013.01);
(Continued)

(58) Field of Classification Search
CPC ................... C23C 16/52; C23C 14/545; G01J 2009/0211; G01N 2021/8427
(Continued)

(56) References Cited

U.S. PATENT DOCUMENTS 5,387,309 A * 2/1995 Bobel ................ G01B 11/0675
117/85
8,122,849 B2 * 2/2012 Clarke ...................... A61J 3/00
118/668
(Continued)

FOREIGN PATENT DOCUMENTS

EP 1 958 620 B1 4/2012
WO WO 2010011833 A1 1/2010

*Primary Examiner* — Cachet Sellman
(74) *Attorney, Agent, or Firm* — Robert A. Blaha; Smith Tempel Blaha LLC

(57) ABSTRACT

A method and a device for monitoring a property of a coating of a solid dosage form during a coating process forming the coating of the solid dosage form are provided. The device comprises a coating apparatus configured for forming the coating on the solid dosage form, and a monitoring apparatus configured for monitoring the property of the coating of the solid dosage form in process, wherein at least a part of the monitoring apparatus is located so as to have insight in an interior of the coating apparatus, the interior accommodating the solid dosage form to be coated and a precursor for forming the coating, and wherein the monitoring apparatus is configured for monitoring the property of the coating of the solid dosage form simultaneously with and during a coating process using low coherence interferometry.

20 Claims, 7 Drawing Sheets

(51) Int. Cl.
*G01B 11/06* (2006.01)
*G01N 21/47* (2006.01)
*G01N 21/95* (2006.01)
*G01B 9/02* (2006.01)

(52) U.S. Cl.
CPC ...... *G01B 11/0675* (2013.01); *G01B 11/0683* (2013.01); *G01N 21/4795* (2013.01); *G01N 21/8422* (2013.01); *G01N 21/9508* (2013.01); *A61J 2200/70* (2013.01); *G01N 2021/8427* (2013.01)

(58) Field of Classification Search
USPC .................... 427/2.14, 7, 8, 2.15, 212, 9, 10
See application file for complete search history.

(56) References Cited

U.S. PATENT DOCUMENTS

| | | | | |
|---|---|---|---|---|
| 2001/0052986 A1* | 12/2001 | Nantel | ................... | G01G 9/005 356/625 |
| 2004/0057650 A1* | 3/2004 | Folestad | ................... | G01J 3/02 385/14 |
| 2010/0294927 A1 | 11/2010 | Nelson et al. | | |
| 2011/0026010 A1* | 2/2011 | Walker | ............... | G01N 21/4795 356/51 |
| 2011/0043820 A1* | 2/2011 | Sansom | ............ | G01B 11/0616 356/503 |
| 2011/0117266 A1* | 5/2011 | Marron | ................... | B05D 1/28 427/2.1 |

* cited by examiner

DEVICE AND METHOD FOR MONITORING A PROPERTY OF A COATING OF A SOLID DOSAGE FORM DURING A COATING OF THE SOLID DOSAGE FORM

CROSS REFERENCE TO RELATED APPLICATION

This application claims the benefit of the filing date of British Patent Application No. 1307734.2 filed 30 Apr. 2013, the disclosure of which is hereby incorporated herein by reference.

TECHNICAL FIELD

The invention relates to a method for monitoring a property of a coating of a solid dosage form during a coating process forming the coating of the solid dosage form. The invention further relates to a device for monitoring a property of a coating of a solid dosage form during a coating process forming the coating of the solid dosage form.

BACKGROUND

Solid dosage forms such as tablets, pellets, capsules and the like are covered by a coating if required. The reasons why solid dosage forms may be covered by a coating are manifold. For instance, a coating may permit to provide a solid dosage form which is resistant to gastric juice. Further, a coating may provide the possibility to modify a release of an ingredient comprised in the solid dosage form. For example, the release of the ingredient comprised in the solid dosage form may be retarded or delayed with respect to an uncoated solid dosage form. Additionally, a coating may prevent that the solid dosage form is damaged. Also, a coating may reduce or even prevent that an ingredient or a substance of a solid dosage form undergoes a chemical reaction, for example, due to contact with air, humidity or a chemical substance. Moreover, some ingredients of a solid dosage form may have a displeasing taste which may be masked by a coating. Further, coatings may also be used in order to maintain an expiration date of a solid dosage form. In order to fulfill these requirements, the coating needs to be applied with a certain thickness, homogeneity and/or quality. For example, if a coating layer is not thick enough, the coating may crack upon contact with another solid dosage form or a container or the solid dosage form may not be resistant to gastric juice.

In order to determine a thickness of a coating, the thickness of the coating may be measured after the coating process is finished, for example by weighing the solid dosage form before and after the coating is formed on the solid dosage form and determining the percentage of the weight gain. Alternatively, the thickness of a coating on a solid dosage form may be determined with a spectroscopy method, for example near infrared or Raman spectroscopy. Although near infrared or Raman spectroscopy may be applied during a coating process, these methods need a reference model which allows to connect a measured spectrum to a corresponding coating thickness. For example, a coating thickness corresponding to a certain spectrum may be determined using a scanning electron microscope which, however, may destroy the coating and/or the solid dosage form, particularly chemical compounds in the coating and/or the solid dosage form. Further method for determining a thickness of a coating may be terahertz pulse imaging, magnetic resonance imaging (MRI) or X-ray microcomputed tomography (X$\mu$CT). In particular, the methods know in the prior art may not allow to determine other properties of the coating than the thickness of the coating. Further, the known methods may be too slow and/or not precise enough to be applied during a process forming the coating.

SUMMARY

However, there may be a need to directly determine a quality and/or property of a coating during the coating process forming the coating on the solid dosage form.

According to an exemplary embodiment of the invention, a device and a method are provided which allow for improving a process for forming a coating on a solid dosage form.

According to an exemplary aspect, a method of monitoring a property of a coating of an at least partially solid dosage form during a coating process forming the coating of the solid dosage form is provided. The method comprises forming the coating on the solid dosage form, and during the forming of the coating of the solid dosage form, simultaneously monitoring the property of the coating of the solid dosage form in process, wherein the property of the coating of the solid dosage form is monitored using low coherence interferometry.

According to a further exemplary aspect, a device for coating an at least partially solid dosage form and monitoring a property of the coating of the solid dosage form during a coating process forming the coating of the solid dosage form is provided. The device comprises a coating apparatus configured for forming the coating on the solid dosage form, a monitoring apparatus configured for monitoring the property of the coating of the solid dosage form in process, wherein at least a part of the monitoring apparatus is located so as to have insight in an interior of the coating apparatus, the interior accommodating the solid dosage form to be coated and a precursor for forming the coating, and wherein the monitoring apparatus is configured for monitoring the property of the coating of the solid dosage form simultaneously with and during a coating process using low coherence interferometry.

The term "at least partially solid dosage form" may particularly denote a dosage form which comprises at least a solid outer shell, which is adapted to be administered to a human or an animal. For example, the at least partially solid dosage form may be a tablet having a solid outer shell and a liquid core. Further, the at least partially solid dosage form may be entirely solid. In particular, the solid dosage form may be a tablet, a pellet, a bead, a pill, a capsule, or a suppository. Further, the solid dosage form may comprise an active drug component such as an active pharmaceutical ingredient and/or a nondrug component. The nondrug component may for example be an excipient. For example, the solid dosage form may be a pharmaceutical drug, a dietary supplement, and/or a food product.

The term "coating" may particularly denote a covering that is applied to the surface of an object, for example a solid dosage form. In particular, a coating may comprise one or more layers. Moreover, a coating may also include an active pharmaceutical ingredient. A coating may improve surface properties of the solid dosage form, such as appearance, adhesion, wettability, corrosion resistance, wear resistance, scratch resistance, and storage life. Further, a coating may reduce or prevent a chemical reaction of a substance in the solid dosage form. In particular, a coating may also improve a resistance of a solid dosage form against gastric juice. Further, a coating may provide the possibility to modify a release characteristic of an ingredient comprised in the solid dosage form. Additionally, a coating may be used to mask a displeasing taste of a solid dosage form, particularly a taste of an ingredient of the solid dosage form.

The term "property of a coating" may particularly denote any measurable attribute of a coating. For example, a property of a coating may be a thickness, a uniformity of a coating, a uniformity of a thickness, a homogeneity, a quality of an attachment, a variation, a thickness variation.

The term "in process" may particularly denote that a particular action is performed during an execution of a process. In other words, while a certain process is executed, a particular action is performed simultaneously.

The term "precursor" may particularly denote compound which may form a coating on a solid dosage form upon contact with the solid dosage form. The precursor may particularly be a solid, a liquid, or a gas. Further, the precursor may be adapted in such a manner that the precursor can be sprayed on the dosage forms.

The term "low coherence interferometry" or "LCI" may particularly denote an interferometry method which exploits the special properties of light having a low coherence. Examples for low coherence interferometry may be white light interferometry (WLI) and optical coherence tomography (OCT). Typically, a light source with high spatial and low temporal coherence may be employed. Particular examples for suitable light sources may include, among others, superluminescence diodes, femtosecond lasers, and supercontinuum lasers. In special applications also tunable laser sources may be applied.

Typically, in order to provide solid dosage forms with a coating, the solid dosage forms are placed in a coating apparatus configured for forming a coating on the solid dosage forms. For example, the coating apparatus may comprise a container, in which a bulk of solid dosage forms can be introduced. In particular, the container may comprise a cylindrical or spherical shape. Further, a coating may be applied to the solid dosage forms in the coating apparatus by spraying a coating material on the bulk of solid dosage forms. A uniform distribution of the coating material over the bulk of solid dosage forms may be achieved due to a motion of the coating apparatus. Alternatively, a uniform distribution of the coating material may be achieved by moving the solid dosage forms through the coating material, for example the solid dosage forms may be moved by an air flow in the coating apparatus. In particular, the bulk of solid dosage forms may be moved in such a way that a coating material sprayed on the bulk of solid dosage forms is uniformly distributed on the solid dosage forms. Furthermore, a coating material may alternatively be poured into the coating apparatus. Moreover, a coating material may be applied on the solid dosage forms by dipping the solid dosage forms into the coating material. A property of the coating, for example a thickness of the coating, may depend on a duration of the coating process. In other words, the longer the duration of the coating process the more coating material may be applied to the solid dosage forms. This holds also true for other properties of the coating. For example, uniformity of the coating may be increased if the duration of the coating process is prolonged.

Further, the monitoring of a property of the coating during the coating of the solid dosage form may be performed by a monitoring apparatus configured for monitoring the property. In particular, the monitoring apparatus may be located in such manner that the solid dosage forms can be monitored while the coating process forming the coating on the solid dosage forms is still in progress. For example, at least a part of the monitoring apparatus may be located so as to have insight in an interior of the coating apparatus; particularly the monitoring apparatus may be located so as to have an insight in the coating apparatus through an aperture or an opening in the coating apparatus. Alternatively, at least a part of the monitoring apparatus may be located inside the coating apparatus. In particular, the interior may accommodate the solid dosage form to be coated and a precursor for forming the coating. Further, the monitoring apparatus may be configured for monitoring the property of the coating of the solid dosage form simultaneously with and during a coating process. Moreover, the monitoring apparatus may be adapted in such a way that the property of the coating may be monitored or measured during the coating of the solid dosage form in the coating apparatus. In other words, it may be rendered unnecessary to interrupt a coating process in order to monitor or determine a property of the coating. In particular, it may be an advantage of the described method and device that a property of a coating can be monitored or determined while the process forming the coating is still in progress. Thus, it may be possible to ensure that a coating process is continued until a property of the coating fulfills a predefined criterion. Further, the described method may provide the advantage that a reference model may be omitted and the property of the coating may be directly determined during the process forming the coating on the solid dosage form. This may provide the advantage that an overall quality of a coating can be increased. Further, a process forming the coating may be performed more efficiently if a property of the coating is monitored during the coating process.

In particular, low coherence interferometry may allow monitoring a property of a coating without harming or even destroying the coating. More particularly, low coherence interferometry may be a non-invasive technique for determining or monitoring a property of a coating of a solid dosage form. Low coherence interferometry uses, like every interferometry technique, the wave superposition principle to combine light waves, particularly light waves that are modified by an object to be analyzed, in a way that will cause the result of their combination to extract information from those instantaneous wave fronts. The basic working principle is as follows: when two waves are combined, the resulting wave pattern may be determined by the phase difference between the two waves. In particular, waves that are in phase will undergo constructive interference while waves that are out of phase will undergo destructive interference.

Exemplary Embodiments

Next, further exemplary embodiments of the method will be explained. However, these embodiments also apply to the device.

According to an exemplary embodiment, the property of the coating is monitored in a time resolved manner.

In particular, monitoring the property of the coating in a time resolved manner may provide the advantage that a progress of the property of the coating can be monitored. Further, monitoring the property of a coating in a time resolved manner may render it possible to control a process forming of the coating of the solid dosage form more precisely. For example, time resolved monitoring of the property of the coating may allow for ending a process forming the coating when a predetermined property value, such as a predetermined thickness or a predetermined homogeneity, has been reached.

According to an exemplary embodiment, the property of the coating is monitored in one, two, or three spatial dimensions.

In particular, monitoring the property of the coating in one spatial dimension may allow for a particularly fast and efficient determining of the property. However, in case a higher accuracy of the monitoring is necessary, the property of the coating may also be monitored in two or three spatial dimensions. Depending on the property to be monitored, it may be particularly necessary to monitor the property in more than one spatial dimension. For example, in order to determine the homogeneity of a coating, it may be necessary to monitor the solid dosage form in at least two spatial dimensions. Monitoring the property of the coating in more than one dimension may be achieved by moving or scanning a light beam of an employed monitoring apparatus in more than one spatial dimension. Alternatively, the property of the coating may be monitored in more than one spatial dimension by moving the solid dosage form. For example, a monitoring of a solid dosage form in two spatial dimensions may be achieved by a motion of the solid dosage form caused by an employed coating apparatus.

According to an exemplary embodiment, the low coherence interferometry uses light having a central wavelength which lies between 400 nm and 8000 nm.

Particularly, an employed light source generating the light used in LCI may have a spectral output which is a sub-interval of the interval ranging from 400 nm to 8000 nm. The employed light source may have a high spatial coherence and a low temporal coherence. Further, the light source may be characterized by the central or center wavelength $\lambda_c$ and a bandwidth $\Delta\lambda$. In particular, the central wavelength $\lambda_c$ may be the wavelength which corresponds to a center of an emission spectrum of the light source. For example, for a light source having a Gaussian emission spectrum the central wavelength $\lambda_c$ may correspond to a maximal output of the light source. However, there may be light sources which have an asymmetrical emission spectrum or an emission spectrum having more than one emission peak. The bandwidth $\Delta\lambda$ may particularly be a full width at half maximum (FWHM) of a spectral output of the light source. In particular, the bandwidth $\Delta\lambda$ of the light source may be in the range of a few hundred nanometers, particularly less than a few hundred nanometers. The light source may be chosen depending on the coating material which is used in the coating process forming the coating and/or the property of the coating, which is monitored. For example, the light source may be chosen such that the wavelength of the light source may allow for the light to enter or penetrate into a scattering media such as the coating of the solid dosage form. Moreover, the light source may be chosen such that a resolution of the monitoring apparatus may be increased. For example, an axial resolution of LCI may scale with $\lambda_c^2/\Delta\lambda$, which results in a higher resolution for a shorter central wavelength.

According to an exemplary embodiment, the low coherence interferometry comprises one of the group consisting of a white light interferometry, and an optical coherence tomography.

As noted above, low coherence interferometry is, like every interferometry technique, an interferometry technique which makes use of the wave superposition principle to combine waves in a way that will cause the result of their combination to extract information from those instantaneous wave fronts. The basic working principle is as follows: when two waves combine, the resulting wave pattern may be determined by the phase difference between the two waves. In particular, waves that are in phase will undergo constructive interference while waves that are out of phase will undergo destructive interference. In particular, optical coherence tomography may refer to a two or three dimensional imaging technique, while low coherence light interferometry and white light interferometry may refer to a one dimensional imaging technique. The optical setup for low coherence interferometry such as white light interferometry or OCT may typically consist of an interferometer, for example a Michelson type interferometer. However, also other types of interferometers, such as a Mach-Zehnder interferometer or a Sagnac interferometer, may be employed. More particularly, the light of the light source may be split into a reference and a sample arm and recombined after the light beam in the sample arm has been modified by the sample. The light of the reference arm and the sample arm may interfere with one another when the light beams are recombined. The recombined light may be used to analyze a property of the sample. Alternatively, an autocorrelation signal may be used to analyze the property of the sample. The autocorrelation signal may result from an interference of light reflected from different positions of the sample. Thus, a reference arm of the interferometer may alternatively be omitted.

In particular, a depth-resolved OCT signal may be acquired by any suitable variant of OCT such as Frequency-domain OCT, e.g. spectral-domain OCT and swept-source OCT, or time-domain OCT.

In time-domain OCT, a reference arm in the interferometer may be varied, particularly by moving a mirror in the reference arm. A signal may only be detected when the photons reflected from both interferometer arms, i.e. the reference arm and a signal or measurement arm, have traveled the same optical distance to a detector. Particularly, mechanical instabilities of an interferometer setup and noise may be induced by the mechanical movement of the mirror in the reference.

The OCT signal acquisition in Fourier-domain OCT may offer advantages in terms of imaging speed and sensitivity and may thus enable the application of OCT as an in-line monitoring method or in process monitoring method. In Fourier-domain OCT, the reference arm of the interferometer may be fixed and the interference signal of back-reflected and back-scattered light from the reference mirror and the sample may be detected in a spectrally resolved way. This may either be performed in parallel (spectral-domain OCT) by using a dispersing element and a CCD or CMOS camera or sequentially (swept-source OCT) by scanning a narrow laser line over a broad spectral region. In both approaches the depth information may be accessed by applying an inverse Fourier transform on the acquired interference spectrum.

The employed light source may be chosen in dependence with the employed imaging technique. For example, time-domain OCT and spectral-domain OCT may employ a light source having a broad bandwidth while swept-source OCT may employ a light source having a smaller or narrower bandwidth, which can be swept in wavelength over a rather large range.

According to an exemplary embodiment, the property of the coating is monitored by analyzing an obtained interference pattern of the low coherence interferometry.

In particular, analyzing the obtained interference pattern or obtained signal may depend on the employed variant of LCI. The interference may cause a modulation in the detected or obtained signal. In case of time-domain OCT, an intensity of the signal may be modulated in time. Correspondingly, an intensity of the obtained signal may be modulated in frequency in case of Fourier-domain OCT. A frequency of the modulation may be a function of a difference of a path length between the two interferometer arms. Thus, the frequency of the modulation may describe the depth from which the light may be scattered.

In particular, there may be two methods for obtaining an interference pattern in case of Fourier-domain OCT, the spectral domain method and the swept-source method. In the spectral-domain method, a broad band light source may be employed and an entire spectrum may be recorded in parallel, for example by using a spectrometer in combination with a line camera or line sensor. In the swept-source method, a laser light source having smaller or narrower bandwidth, which can be swept in wavelength over a rather large range, may be used. In this case, the spectrum may be recorded with a photo detector, particularly one wavelength after the other. In both methods, the spectral domain method and the swept-source method, the obtained interference pattern may be inverted, i.e. the obtained interference pattern may be transferred into k space or frequency space. Further, the transferred interference pattern may be linearized, if necessary, and an inverse Fourier transform may be applied.

Furthermore, in case of Fourier-domain OCT, the obtained interference pattern may also be denoted as channeled spectrum. The term "channeled spectrum" may particularly denote an intensity pattern that may result from an interference of the light beams in a reference arm and a sample arm of an interferometer and dispersion of the interfered beam as function of wavelength. For a point source that may be imaged by two apertures that are slightly out of phase, the channeled spectrum is a fringe pattern with higher intensity at those wavelengths that are an integer number of wavelengths out of phase, and lower intensity for wavelengths that destructively interfere.

According to an exemplary embodiment, the property of the coating is monitored by analyzing an inverse Fourier transform of an obtained interference pattern of the low coherence interferometry.

In particular, a frequency space and a position space may be connected via a Fourier transform. Applying a Fourier transform or an inverse Fourier Transform to an obtained channeled spectrum or obtained interference pattern of the low coherence interferometry may allow for a simple and efficient way of analyzing the property of the coating.

According to an exemplary embodiment, the property of the coating is one of the group consisting of a thickness of the coating, a homogeneity of the coating, a thickness variation of the coating or a quality of an attachment of the coating to the solid dosage form.

For example, it may be necessary to ensure a certain thickness of a coating in order to ensure a particular quality feature for a solid dosage form, such as appearance, corrosion resistance, wear resistance, scratch resistance, and/or storage life. Furthermore, a homogeneity of the coating may also improve a quality of the coating. In particular, quality of the coating may be better the less the thickness of the coating varies. More particularly, there may be a need to reduce a variation of a coating thickness to a minimum. Another property of a coating may be a quality of an attachment of the coating to the solid dosage form. Depending on the material and/or substance of the solid dosage form it may be necessary to monitor how a coating attaches to the solid dosage form. In particular, in some case it may be necessary to monitor a forming of a coating during the coating process in order to ensure that the coating attaches to the solid dosage forms.

According to an exemplary embodiment, the method further comprises classifying the solid dosage forms in accordance with the result of the monitoring, particularly separating the solid dosage forms having a monitored property failing to comply with a predefined criterion.

In particular, solid dosage forms failing to comply with a predefined criterion of the property of the coating may be separated. This may allow separating or sorting a bulk of solid dosage forms in solid dosage forms having a property of the coating which complies with the predefined criterion and solid dosage forms having a property which may not comply with the predefined criterion. Such a sorting may allow fulfilling certain quality requirements since the solid dosage forms which may not comply with the predefined criterion may be separated from the solid dosage forms complying with the predefined criterion. The predefined criterion may relate to the monitored property of the coating.

According to an exemplary embodiment, the method further comprises post-processing selectively the solid dosage forms having a property failing to comply with the predefined criterion.

In particular, the sorted solid dosage form may be post-processed. By selectively post-processing the solid dosage form having a property failing to comply with the predefined criterion a certain quality of the solid dosage form may be maintained. For example, the solid dosage forms having a property failing to comply with the predefined criterion may be removed from the bulk of solid dosage forms. Another possibility may be to repeat the coating process for all solid dosage forms having a property failing to comply with the predefined criterion. Also it may be possible to apply an alternative coating process suited to correct or mend the coating of the solid dosage form.

According to an exemplary embodiment, the post-processing is one of the group consisting of repeating the coating process for the solid dosage form having a property failing to comply with the predefined criterion, and removing the solid dosage form having a property failing to comply with the predefined criterion.

According to an exemplary embodiment, a starting point of the monitoring of the property of the coating is controlled in accordance with a characteristic of the coating process forming the coating.

In particular, the characteristic of the coating process may be a characteristic of an employed coating apparatus, such as a rotation speed. More particularly, a coating apparatus may be rotated in order to evenly distribute a coating material over a bulk of solid dosage forms located in the coating apparatus for being coated. Further, the characteristic of the coating process may be a presence of solid dosage forms in the employed coating apparatus. This may provide the advantage that a monitoring may only be started when solid dosage forms are present in an employed coating apparatus. The starting point of the monitoring may be indicated by a signal, particularly a trigger signal, indicating that a predefined characteristic of the coating process forming the coating is fulfilled.

According to an exemplary embodiment, an ending point of the coating process forming the coating of the solid dosage form is controlled in accordance with the monitored property of the coating.

In particular, a coating process may be performed until a monitored property may fulfill a predefined criterion. A predefined criterion may define an ending point for the coating process forming the coating. More particularly, a signal may be generated upon fulfilling the predefined criterion, which may be sent to an employed coating apparatus performing the process forming the coating. For example, the coating process may be performed until the coating has a certain thickness or fulfills another predefined criterion. Thus, the ending point of the coating process may depend on the thickness or the other predefined criterion of the coating.

According to an exemplary embodiment, the method further comprises adapting the monitoring of the property of the coating of the solid dosage form in accordance with a characteristic of the coating process forming the coating.

The characteristic of the coating process forming the coating may be a rotation speed of an employed coating apparatus, an airflow in an employed coating apparatus, an air temperature, an amount of precursor in the employed coating apparatus. In particular, adapting the monitoring of the property of the coating of the solid dosage form may be adapting a light intensity of a light source employed in the LCI, adapting an exposure time of an employed detector in the LCI and/or adapting an adjustable aperture. For example, an exposure time of an employed detector may be adapted or adjusted to a diameter of an opening through which the monitoring of the property of the coating is performed and/or the rotation speed of an employed coating apparatus. Particularly, adapting the monitoring of the property of the coating of the solid dosage form based on the characteristic of the coating process may provide the advantage that a quality of a monitoring may be improved.

According to an exemplary embodiment, the monitoring of the property of the coating is performed during the presence of the solid dosage form within a coating apparatus within which a precursor of the coating is present.

In particular, the low coherence interferometry used for monitoring the property of the coating may be adapted in such a manner that the property of the coating can be monitored while the solid dosage forms are present within a coating apparatus. More particularly, the employed precursor may be transparent for a used wavelength of the low coherence interferometry. Further, the coating apparatus may at least be partially transparent for a light beam of the low coherence interferometry. For example, the coating apparatus may comprise a part which is made from a transparent material, in particular a material which is transparent for the employed light. A light source for the low coherence interferometry may be chosen in such a manner that the wavelength of the light source is not absorbed by a precursor medium and/or a material of the coating apparatus. Also, a density of the precursor may be adapted in such a way that the light of the low coherence interferometry is particularly disturbed.

Next, further exemplary embodiments of the device will be explained. However, these embodiments also apply to the method.

According to an exemplary embodiment, the device further comprises a quality determining unit configured for determining information indicative of a quality of a coating of a solid dosage form by comparing the monitored property of the coating with a predefined criterion.

In particular, the quality determining unit may comprise a database having a list comprising at least one predefined criterion. Moreover, the predefined criterion may depend on a type of coating material and/or a substance of the solid dosage form. The quality determining unit may obtain data representing the property of the coating of the solid dosage form from the monitoring unit. Further, the quality determining unit may be configured for sorting the solid dosage forms. A possible sorting parameter may be a result of a comparison of the monitored property with the predefined criterion. In particular, the quality determining unit may be configured for sorting the solid dosage forms in a part of solid dosage forms complying with the predefined criterion and a part of solid dosage forms failing to comply with the predefined criterion.

According to an exemplary embodiment, the device further comprises a post-processing unit configured for post-processing the solid dosage form having a property failing to comply with the predefined criterion.

In particular, a post-processing unit may be configured for performing a post-processing process. For example, a post-processing process may be to remove a solid dosage failing to comply with the predefined criterion or to repeat the coating process. Alternatively, the post-processing process may an alternative coating process, for example a coating process with a different coating material or in a different coating apparatus.

According to an exemplary embodiment, at least a part of the monitoring apparatus is located within the coating apparatus, wherein the part of the monitoring apparatus is located particularly in a mantle of the coating apparatus.

In particular, a coating apparatus may comprise a container in which a bulk of solid dosage forms may be fillable. More particularly, the container may have a cylindrical or a spherical shape. Furthermore, the container of the coating apparatus may comprise at least one hole or recess in which at least a part of the monitoring apparatus is locatable.

According to an exemplary embodiment, the coating apparatus comprises at least one of the group consisting of a rotating drum coating system, a tumble coating system, and a fluid bed coating system.

In particular, rotating drum coating systems, tumble coating systems and fluid bed coating systems may be standard coating systems employed in processes forming a coating on a solid dosage form.

According to an exemplary embodiment, the monitoring apparatus is further configured for starting the monitoring of the property of the coating in accordance with a characteristic of the coating apparatus.

In particular, the characteristic of the employed coating apparatus may be a rotation speed, a position of an opening through which the monitoring apparatus may have insight into the coating apparatus, and/or a diameter of such an opening. Further, the characteristic of the coating process may be a presence of solid dosage forms in the employed coating apparatus. This may provide the advantage that a monitoring may only be started when solid dosage forms are present in an employed coating apparatus. The starting point of the monitoring may be indicated by a signal, particularly a trigger signal, indicating that a predefined characteristic of the coating process forming the coating is fulfilled.

According to an exemplary embodiment, the monitoring apparatus is further configured for generating a signal indicating the property of the coating, and the coating apparatus is further configured for ending the coating process forming the coating of the solid dosage form based on the signal.

In particular, the signal may be a trigger signal indicating for example that a predefined criterion of the property may be fulfilled. By ending a coating process forming the coating based on a signal indicating the property of the coating, it may be possible to provide a faster and/or more efficient coating process while maintaining a certain quality standard. A quality determining unit may alternatively generate the signal indicating the property of the coating, in case the device for coating the at least partially solid dosage form and monitoring a property of the coating of the solid dosage form during a coating process forming the coating comprises a quality determining unit.

According to an exemplary embodiment, the monitoring apparatus is further configured for adapting the monitoring of the property of the coating of the solid dosage form based on a characteristic of the coating apparatus.

The characteristic of the coating apparatus may be a rotation speed, a position of an opening through which the monitoring apparatus may have insight into the coating apparatus, and/or a diameter of such an opening. In particular, the monitoring apparatus may be configured for adapting a light intensity of a light source employed in the LCI, an exposure time of an employed detector in the LCI and/or an adjustable aperture in the monitoring apparatus based on the characteristic of the coating apparatus. For example, an exposure time of an employed detector may be adapted or adjusted to a diameter of an opening through which the monitoring apparatus may have insight into the coating apparatus and/or the rotation speed of the coating apparatus. Particularly, adapting the monitoring of the property of the coating of the solid dosage form based on the characteristic of the coating apparatus may provide the advantage that a quality of a monitoring may be improved.

According to an exemplary embodiment, the monitoring apparatus and the coating apparatus are arranged relatively to one another and are configured so that the solid dosage form is moved during the coating process within the coating apparatus and thereby moves into a field of view of the monitoring apparatus, whereby the monitoring apparatus is enabled to perform the low coherence interferometry on the solid dosage form while remaining within the field of view.

In particular, an outer part of the coating apparatus may be configured in such a manner that the coating apparatus may be transparent for an employed wavelength of the monitoring apparatus.

According to an exemplary embodiment a program element is provided, which, when being executed by a processor, is adapted to control and/or carry out a method according to an exemplary aspect of the invention. Further the program element may be adapted, when being executed by a processor, to monitor a property of a coating. Moreover, the program element may be adapted, when being executed by a processor, to control a low coherence interferometry for monitoring a property of a coating.

The program element may be implemented as a computer readable command code in any suitable programming language such as JAVA, C++ etc. The program element may be stored on a computer readable medium such as CD-ROM, DVD, Blue-ray Disk, removable drive, volatile and non-volatile memory etc. Further, the program element may be provided in a network, for example the Internet, and may be downloaded from a user on demand.

According to an exemplary embodiment, a computer-readable medium, in which a computer program is stored which, when being executed by a processor, is adapted to control and/or carry out a method according to an exemplary aspect of the invention.

The aspects defined above and further aspects of the invention are apparent from the examples of embodiment to be described hereinafter and are explained with reference to these examples of embodiment.

The invention will be described in more detail hereinafter with reference to examples of embodiment but to which the invention is not limited.

BRIEF DESCRIPTION OF THE DRAWINGS

The illustration in the drawing is schematically. In different drawings, similar or identical elements are provided with the same reference signs.

DETAILED DESCRIPTION

Figure 1:
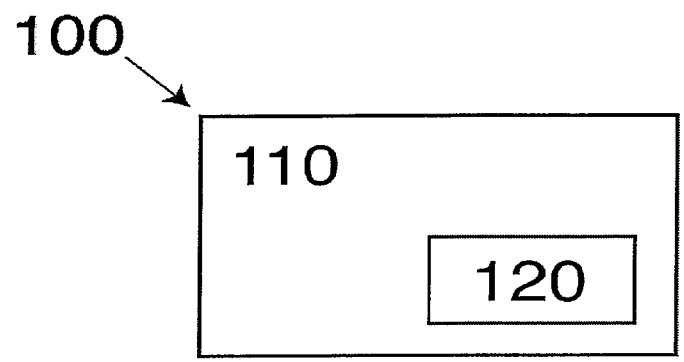
FIG. 1 illustrates a schematic view of a device for monitoring a property of a coating of a solid dosage form according to an exemplary embodiment.

In the following, referring to FIG. 1, a device 100 for monitoring a property of a coating 104 of a solid dosage form 102 during a coating process forming the coating 104 of the solid dosage form according to an exemplary embodiment will be explained.

The device 100 for monitoring a property of a coating 104 of a solid dosage form 102 during a coating process comprises a coating apparatus 110 configured for coating the solid dosage form, and monitoring apparatus 120 configured for monitoring the property of the coating of the solid dosage form in process. In particular, the monitoring apparatus 120 is placed in such a way that at least a part of the monitoring apparatus 120 is located in the coating apparatus 110. For example, the coating apparatus may comprise a container in which the solid dosage form may be introduced during a coating process. The monitoring apparatus 120 may be placed in a hole or a recess formed in a mantle of the container of the coating apparatus 110. The monitoring apparatus 120 is configured performing a low coherence interferometry measurement in order to monitor the property of the coating 104 of the solid dosage form 102 during a coating process using low coherence interferometry. In particular, the coating apparatus may be a standard coating apparatus such as a rotating drum coating system or a fluid bed coating system.

Figure 2:
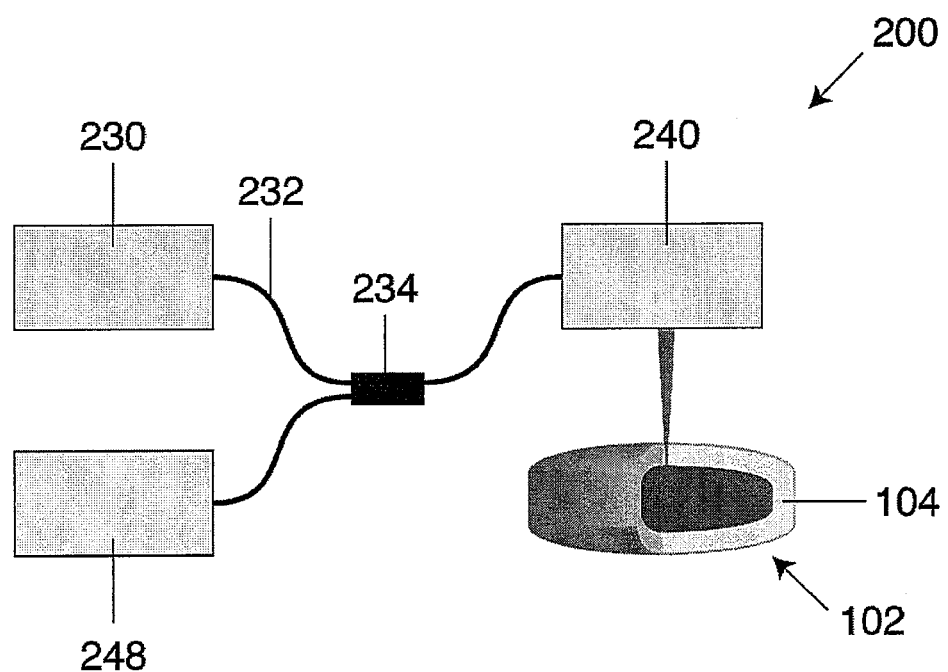
FIG. 2 shows a schematic setup of a low coherence interferometry measurement.

In the following, referring to FIG. 2, a schematic setup 200 for a low coherence interferometry measurement according to an exemplary embodiment will be explained.

The setup 200 comprises a light source 230 having a high spatial coherence and a low temporal coherence. The light obtained from the light source 230 may be coupled into an optical fiber 232. Alternatively, the light from the light 230 may be guided freely, this means that the optical fiber 232 may be omitted. The light is guided towards a directional element 234.

The directional element 234 is configured in such a way that at least a part of the light travelling backwards, that is the light which is reflected back towards the light source, is separated from the light originating from the light source 230. Thus, the back reflected light will not be directed towards the light source 230. Instead, the back reflected light may be directed into an analyzing unit 248. There may be several possible setups as how to implement such a directional element. For example, the directional element 234 may be based on a beam splitter, a polarizing beam splitter and a wave plate, a Faraday rotator and/or an optical isolator. Depending on the directional element, it may happen that light is coupled back into the light source. Depending on the light source, suitable protection measures may have to be taken. For example, the light source may be protected from retro-reflected light by an optical isolator.

After passing the directional element 234, the light is directed towards an interferometer 240. In particular, the light may be shaped by a beam shaping element, such as a lens and/or a telescope, in order to provide a collimated light beam, a focused light beam or a divergent light beam. The employed interferometer obtains information about a property of a coating 104 of a solid dosage form 102 by interfering light scattered from the solid dosage form with a reference beam. Alternatively, the information may be obtained by evaluating an autocorrelation signal resulting from an interference of light reflected from different positions of the solid dosage form 102. In this case, the reference beam may be omitted. Depending on the employed interferometer, the light beam carrying the interference signal may be superimposed with the light coming from the light source 230. In order to analyze the interference signal and extract the obtained information, the two beams, that is the incoming light beam and the light beam carrying the interference signal, are separated from one another by the directional element 234, for example by a beam splitter. Further, depending on a specific implementation of the directional element 234, there may be a risk that a part of the reflected light reaches the light source. This may cause problems with the light source depending on the light source. This may be prevented by an optical isolator or optical diode through which light may only travel in one direction. The separated light beam carrying the interference signal is then guided towards an analyzing unit 248 which analyzes the interference signal and extracts the information, particularly depth information, about the monitored property of the coating.

In the following, referring to FIG. 3, a schematic setup 300 for a low coherence interferometry measurement in one dimension according to another exemplary embodiment will be explained.

The setup 300 comprises a light source 330. The light obtained from the light source 330 is coupled into an optical fiber 332. As described above, the optical fiber 332 may alternatively be omitted. The optical fiber 332 is connected to a directional element 334 and guided through a further optical fiber until it is coupled out of the further optical fiber by a fiber focuser 336 and directed onto a beam splitter 338. The fiber focuser 336 is particularly configured for providing a focused light beam. The beam splitter 338 splits the light beam from the light source 330 into two interferometer arms, 340 and 342. The light beam in interferometer arm 340 is a reference beam which is reflected by a retro-reflecting mirror 346. The mirror 346 is adjusted in such a way that the reflected beam is coupled back into the optical fiber by the fiber focuser 336.

As described above, the directional element 334 is configured in such a way that the light travelling backwards is separated from the light originating from the light source 330. Thus, at least a part of the back reflected light may not be coupled into the light source 330. Instead, at least a part of the back reflected light is coupled into an analyzing unit 348.

The second light beam in interferometer arm 342 is reflected by the beam splitter 338 onto a solid dosage form 102. The solid dosage form 102 also reflects at least a part of the light of the light beam 342. The two reflected light beams from the two interferometer arms 340 and 342 are recombined by the beam splitter 338 and thus brought into interference.

The recombined beams of the two interferometer arms 340 and 342 are separated from the incoming light beam by the directional element 334 as described above and directed towards an analyzing unit 348. The analyzing unit 348 analyzes the interference signal and extracts the information, particularly the information in the axial direction, about the monitored property of the coating 104. Moreover, by moving the solid dosage form 102 in a radial direction perpendicular to the axial direction, information about the monitored property of the coating 104 of the solid dosage form may be obtained in two dimensions.

Figure 4:
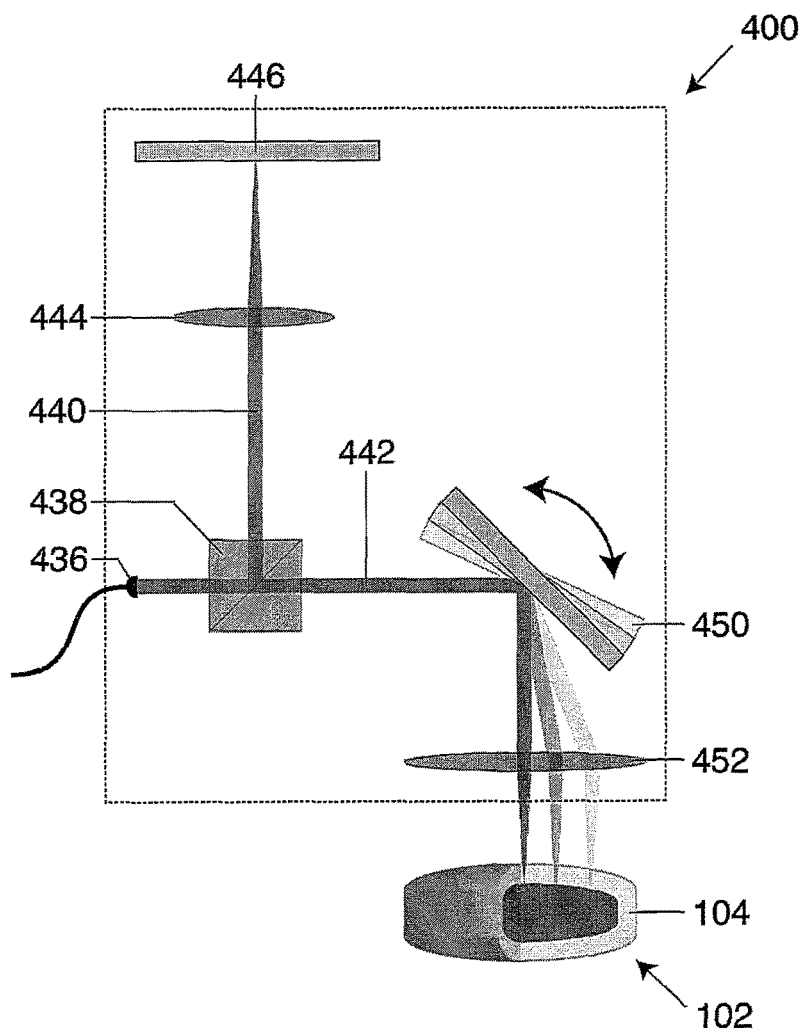
FIG. 4 shows a schematic setup for an optical coherence interferometry measurement in two dimensions.

In the following, referring to FIG. 4, a schematic setup for an optical coherence interferometry measurement in two dimensions according to another exemplary embodiment will be explained.

Figure 3:
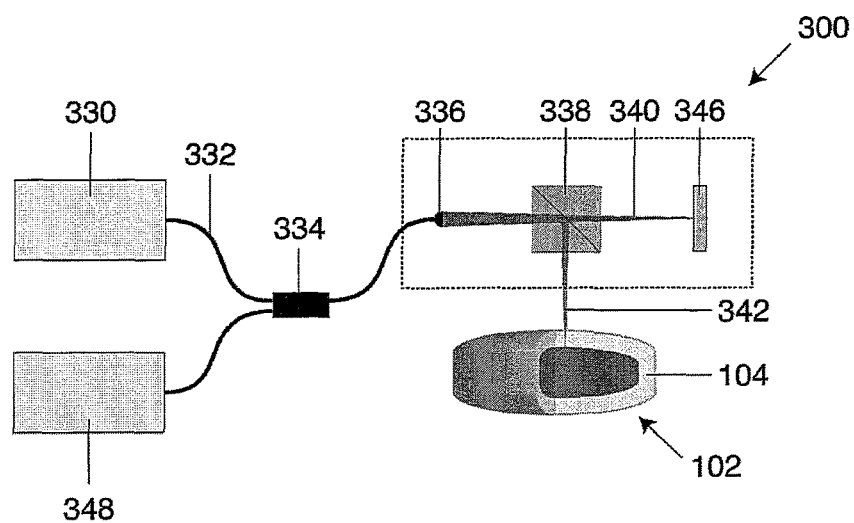
FIG. 3 shows a schematic setup for a low coherence interferometry measurement in one dimension.

The setup 400 may have a similar light source setup as the setup 300 shown in FIG. 3. The light from the light source is coupled out of an optical fiber by a fiber collimator 436 and onto a beam splitter 438. The fiber collimator 436 is configured for providing a collimated light beam. The beam splitter 438 then splits the light beam into two interferometer arms, 440 and 442. The light beam in interferometer arm 440 is a reference beam which is focused by a lens 444 onto a retro-reflecting mirror 446. Alternatively, the lens 444 may also be omitted. In such a case, an element for dispersion compensation may be put into the light beam 440 instead of the lens 444. Further, the mirror 446 is adjusted in such a way that the reflected beam is coupled back into the optical fiber by the fiber collimator 436.

The second light beam in interferometer arm 442 is focused by a further lens 452 via a galvanometer mirror 450 onto a solid dosage form 102. The galvanometer mirror is configured to move the focused light beam over the solid dosage form. The solid dosage form 102 also reflects at least a part of the light of the light beam 442. The two reflected light beams from the two interferometer arms 440 and 442 are recombined by the beam splitter 438 and thus brought into interference. By analyzing the light beam carrying the interference signal, information about a property of a coating 104 of the solid dosage 102 in two dimensions, i.e. the axial dimension and a first transversal dimension, can be extracted. Moreover, if the solid dosage form is moved in a second transversal dimension perpendicular to the first transversal dimension, the property of the coating 104 may be monitored in three spatial dimensions.

Figure 5:
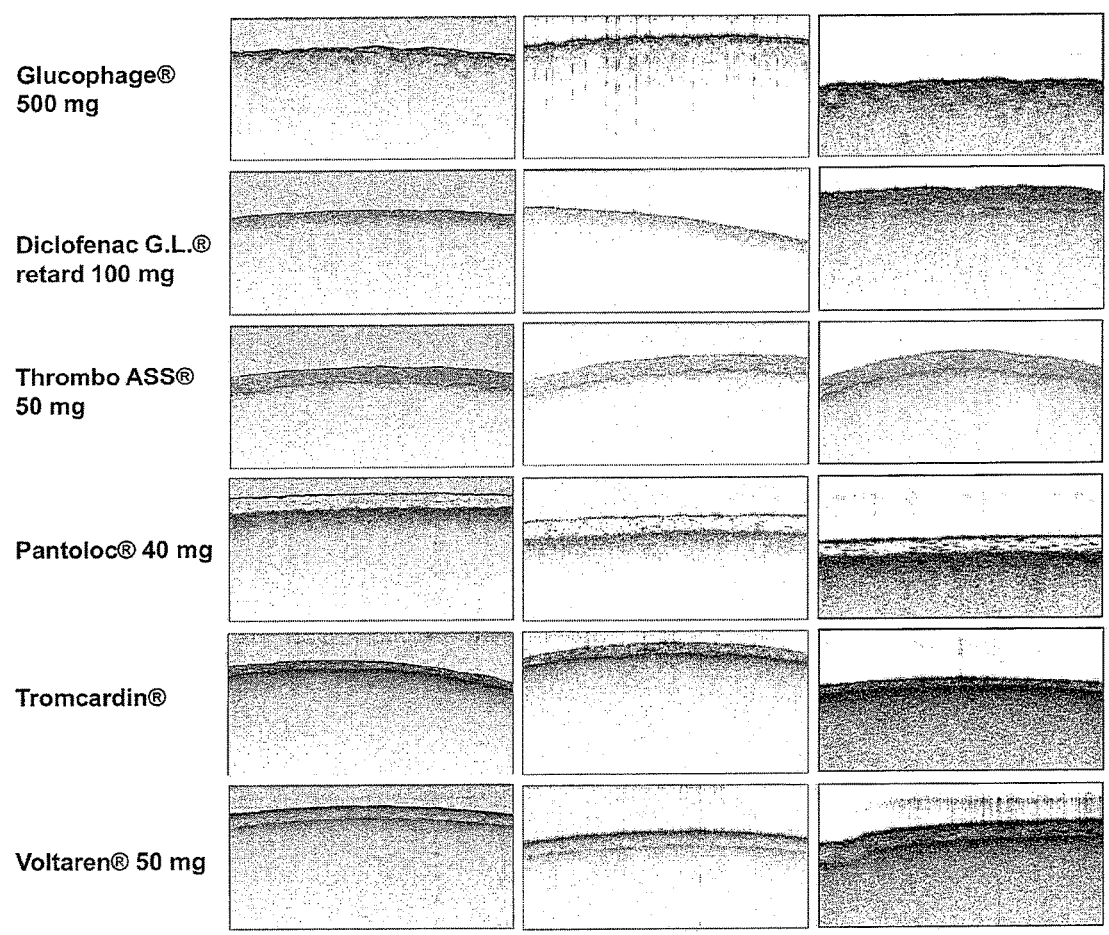
FIG. 5 shows OCT images of a coating of several solid dosage forms comprising different pharmaceutical substances.

In the following, referring to FIG. 5, a table of OCT images of a coating of several solid dosage forms comprising different pharmaceutical substances will be described.

The type of solid dosage form shown in each respective row is written in the first column. Images are shown in the second column, which are obtained with a supercontinuum light source with a center wavelength of 820 nm and a bandwidth (FWHM) of 170 nm. The images in the third column are obtained with a superluminescent diode light source with a center wavelength of 830 nm and a FWHM bandwidth of 62 nm. The images in the fourth column are obtained with a superluminescent diode light source with a center wavelength of 1325 nm and a FWHM bandwidth of 150 nm. Each OCT image shown in FIG. 5 has a dimension of 2×1 mm$^2$ in air.

Figure 6:
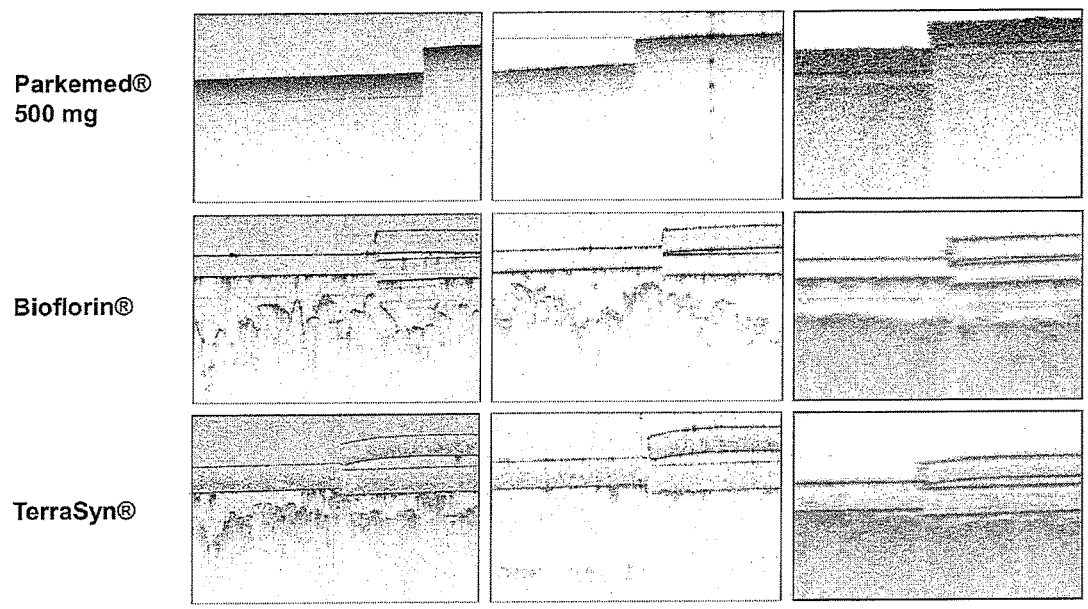
FIG. 6 shows OCT images of a coating of several solid dosage forms in form of capsules comprising different pharmaceutical substances.

In the following, referring to FIG. 6, a table of OCT images of a coating of several solid dosage forms in form of capsules comprising different pharmaceutical substances will be described.

The type of solid dosage form shown in each respective row is written in the first column. Images are shown in the second column, which are obtained with a supercontinuum light source with a center wavelength of 820 nm and a bandwidth (FWHM) of 170 nm. The images in the third column are obtained with superluminescent diode light source with a center wavelength of 830 nm and a FWHM bandwidth of 62 nm. The images in the fourth column are obtained with a superluminescent diode light source light source with a center wavelength of 1325 nm and a FWHM bandwidth of 150 nm. Each OCT image shown in FIG. 6 has a dimension of 2×1.3 mm$^2$ in air.

In the following, referring to FIG. 7, a series of OCT images illustrating a progress of a coating process will be described.

Figure 7:
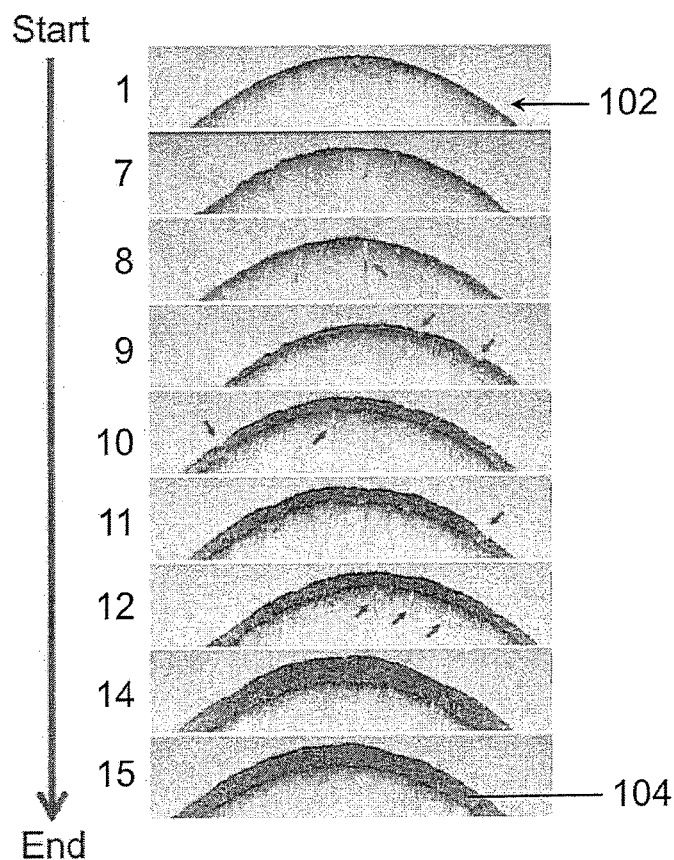
FIG. 7 shows a series of OCT images illustrating a progress of a coating process.

The top image of the series of images shown in FIG. 7 shows the start of the coating process. As can be seen the applied coating 104 is merely a thin line at an edge of the solid dosage form 102. In this case, the solid dosage form is a tablet. During the progress of the coating process the thickness of the coating 104 increases, as can be clearly seen by comparing image 1 with image 15. Further, the obtained images also allow monitoring uniformity and/or homogeneity of the applied coating. The arrows shown in images 8 to 12 indicate positions where the coating may comprise slight defects with respect to uniformity and/or homogeneity of the coating. Each OCT image shown in FIG. 7 has a dimension of 4.3×0.36 mm$^2$ in air.

In the following, referring to FIGS. 8 and 9, a series of optical coherence tomography images illustrating a progress of a coating process of solid dosage forms in form of pellets will be described.

Figure 8:
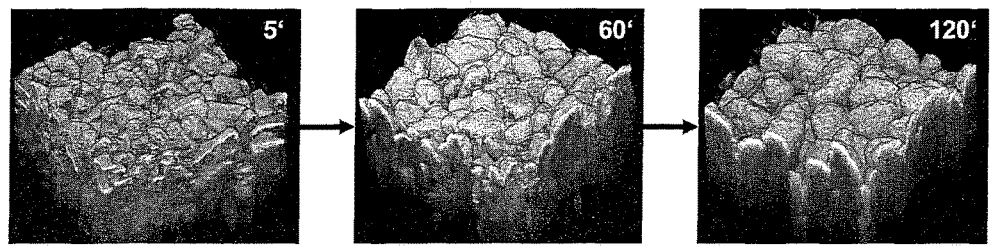
FIGS. 8 and 9 show a series of optical coherence tomography images illustrating a progress of a coating process of solid dosage forms in form of pellets.
Figure 9:
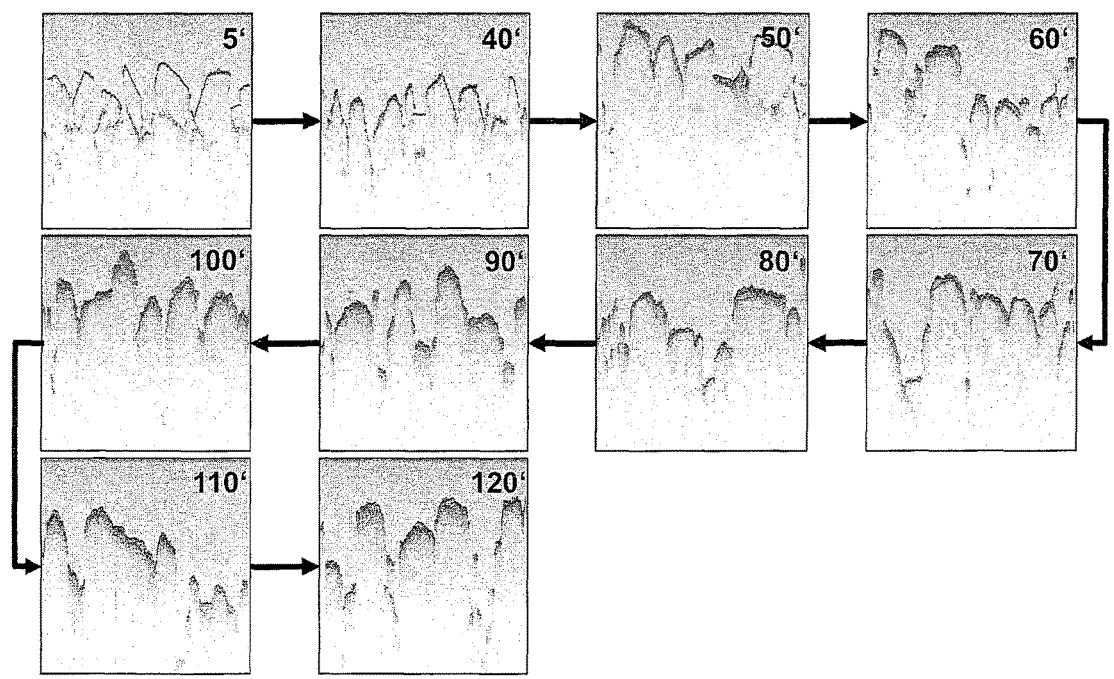

Each image in FIG. 8 shows an area of 2.5×2.5×2.5 mm$^3$ in air. The shown pellets are coated in a fluidized bed coater. The pellets were coated in the coating apparatus for a duration of 120 minutes. FIG. 9 shows two dimensional cross section images obtained at different stages of the coating process. It can be clearly seen from the images shown in FIG. 9 how the thickness of the coating increases with increasing duration of the coating process. Each OCT image shown in FIG. 9 has a dimension of 2.14×1.3 mm$^2$ in air.

In the following, referring to FIG. 10, an optical coherence tomography image in two dimensions illustrating a progress of a coating process of solid dosage forms in form of pellets will be described.

Figure 10:
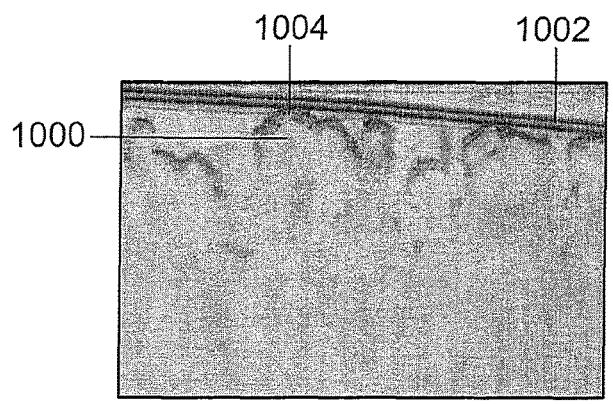
FIG. 10 shows an OCT image in two dimensions of solid dosage forms in form of pellets.

The image in FIG. 10 shows an area of 2.9×1.9 mm$^2$ in air. The shown pellets 1000 are film-coated. The obtained thickness of the coating 1004 is approximately 70 μm. Further, the pellets are placed inside a protective foil 1002 as can be seen in the image shown in FIG. 10.

In the following, referring to FIG. 11, a further series of optical coherence tomography images in two dimensions illustrating a progress of a coating process of solid dosage forms in a fluidized bed coater will be described.

Figure 11:
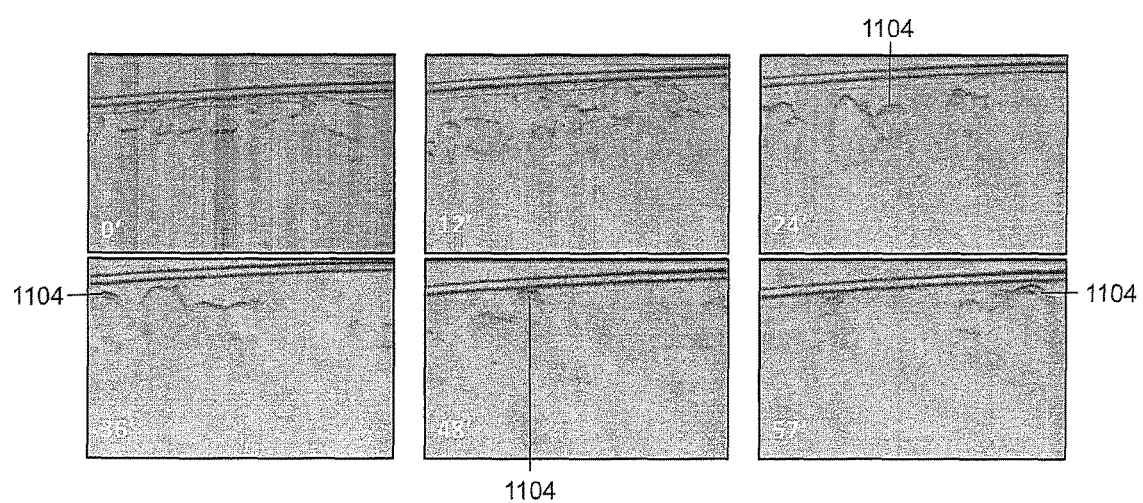
FIG. 11 shows a further series of optical coherence tomography images in two dimensions illustrating a progress of a coating process of solid dosage forms in a fluidized bed coater.

Each image in FIG. 11 shows an area of 2.9×1.9 mm$^2$ in air. The shown solid dosage forms 1000 were coated in the fluidized bed coater for a duration of 57 minutes.

Figure 12:
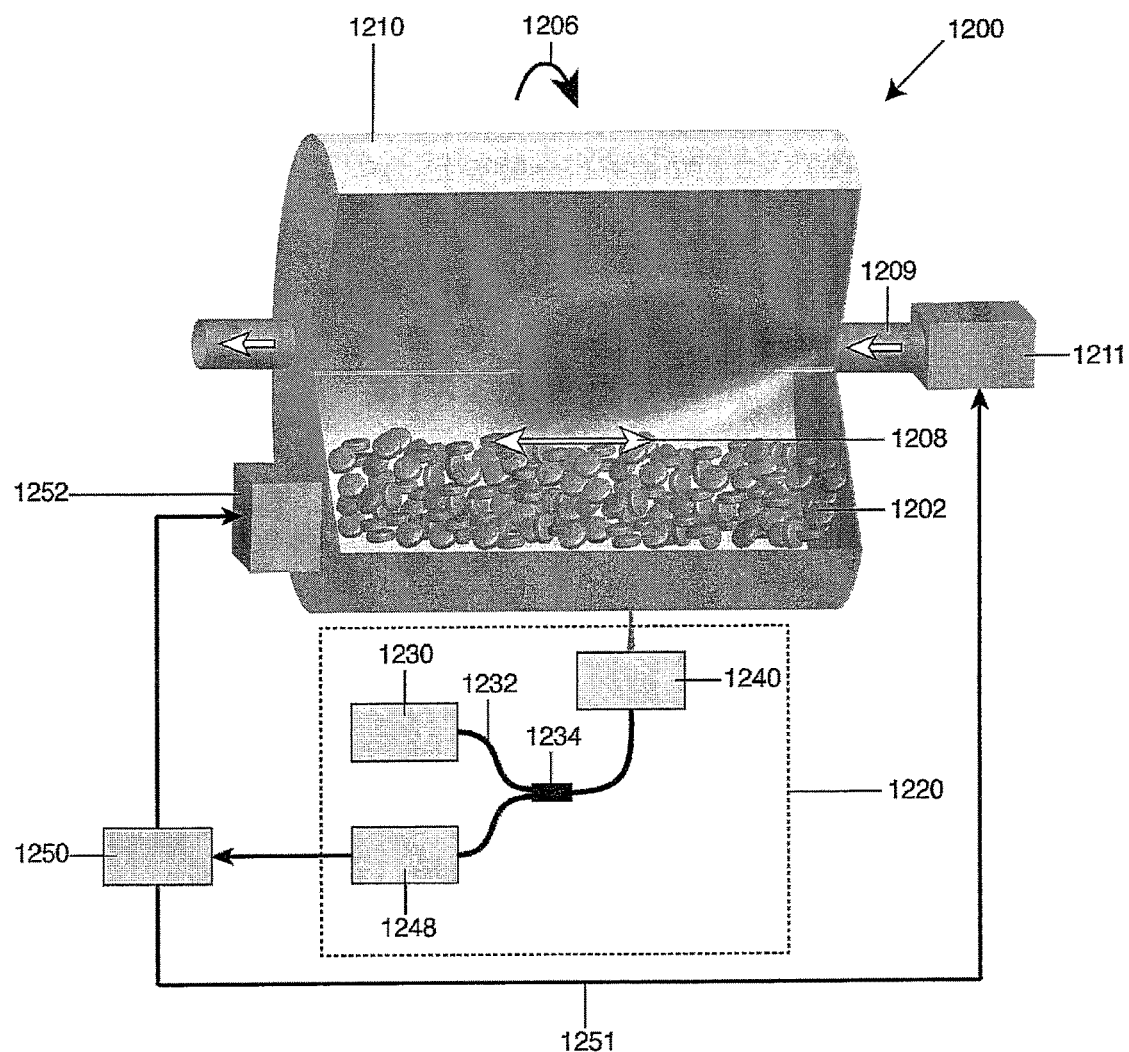
FIG. 12 shows a schematic setup of a device for monitoring a property of a coating of a solid dosage form according to a further exemplary embodiment.

In the following, referring to FIG. 12, a schematic setup of a device for monitoring a property of a coating of a solid dosage form according to a further exemplary embodiment coater will be described.

The device 1200 for monitoring a property of a coating of a solid dosage form 1202 during a process forming the coating comprises a coating apparatus 1210 configured for forming a coating on the solid dosage form 1202. The coating apparatus shown in FIG. 12 is a tumble coating system in which the solid dosage forms are moved by a rotational movement of the tumble coating system. Arrow 1206 indicates the rotational movement of the tumble coating system and arrow 1208 indicates a movement of the solid dosage forms in the tumble coating system. A precursor is supplied to the tumble coating system 1210 from a precursor container 1211 via a supply line 1209 located at one end of the tumble coating system. The finished solid dosage forms are removable from the tumble coating system 1210 from the other end of the tumble coating system.

A monitoring apparatus 1220 is provided, which is configured for monitoring the property of the coating of the solid dosage form during the process forming the coating. In particular, the monitoring apparatus 1220 is placed in such a way that at least a part of the monitoring apparatus 1220 has insight in an interior of the coating apparatus 1210. The monitoring apparatus 1220 is configured performing a low coherence interferometry measurement. In particular, the monitoring apparatus 1220 comprises a light source 1230 and the light from the light source 1230 is directed towards a directional element 1234 which then directs the light to an interferometer setup 1240. The directional element 1234 is described above. The interferometer 1240 may be any suitable interferometer setup, for example a Michelson interferometer. A light beam of the interferometer 1240 is directed onto the solid dosage forms 1202 in the tumble coating system 1210. Therefore, the tumble coating system comprises a container which is at least partly transparent for the light originating from the light source 1230. At least a part of the light of the light beam is reflected or scattered by the solid dosage forms 1202 towards the directional element 1234. The reflected light beam interferes with a reference beam, as described with regard to FIGS. 3 and 4, or, in case a reference beam is omitted in interferometer 1240, with light reflected from different positions of the solid dosage form 1202.

The light beam carrying the interference signal is separated from the incoming light beam by the directional element 1234 as described above and directed towards the analyzing unit 1248. The information obtained by the analyzing unit 1248 is provided to a control unit 1250 which is configured to control the process forming the coating on the solid dosage forms 1202 based on the information obtained by the analyzing unit 1248. Particularly, the analyzing unit 1248 may be adapted to analyze an obtained inference pattern, such as a channeled spectrum of the low coherence interferometry and/or an inverse Fourier transform of a channeled spectrum of the low coherence interferometry. Moreover, the control unit 1250 may be configured to control a characteristic of the coating process forming the coating, such as an amount of precursor supplied to the tumble coating system 1210, as indicated by arrow 1251. Also, the control unit may be configured for stopping a coating process forming the coating. Further, the control unit 1251 may be configured for controlling a driving unit 1252 which is adapted to drive a movement of the coating system, for example the rotational movement indicated by arrow 1206. Further, driving unit 1252 may be adapted to drive an airflow and/or an air temperature.

It should be noted that the term "comprising" does not exclude other elements or steps and the "a" or "an" does not exclude a plurality. Also elements described in association with different embodiments may be combined.

The invention claimed is:

1. A method of monitoring a property of a coating of an at least partially solid dosage form during a coating process forming the coating of the solid dosage form, the method comprising:
    forming the coating on the solid dosage form, and
    during the forming of the coating of the solid dosage form, simultaneously monitoring the property of the coating of the solid dosage form in process,
    wherein the property of the coating of the solid dosage form is monitored by a monitoring apparatus using low coherence interferometry,
    moving the solid dosage form during the coating process into a field of view of the monitoring apparatus.

2. The method according to claim 1, wherein the property of the coating is monitored in a time resolved manner.

3. The method according to claim 1, wherein the property of the coating is monitored in one, two, or three spatial dimensions.

4. The method according to claim 1, wherein the low coherence interferometry uses light having a central wavelength which lies between 400 nm and 8000 nm.

5. The method according to claim 1, wherein the low coherence interferometry comprises one selected from the group consisting of a white light interferometry, and an optical coherence tomography.

6. The method according to claim 1, wherein the property of the coating is monitored by analyzing an obtained interference pattern of the low coherence interferometry.

7. The method according to claim 1, wherein the property of the coating is one selected from the group consisting of a thickness of the coating, a homogeneity of the coating, a thickness variation of the coating or a quality of an attachment of the coating to the solid dosage form.

8. The method according to claim 1, further comprising:
    classifying the solid dosage forms in accordance with the result of the monitoring, particularly separating the solid dosage forms having a monitored property failing to comply with a predefined criterion.

9. The method according to claim 8, further comprising:
    post-processing selectively the solid dosage forms having a property failing to comply with the predefined criterion.

10. The method according to claim 9, wherein the post-processing is one selected from the group consisting of repeating the coating process for the solid dosage form having a property failing to comply with the predefined criterion, and removing the solid dosage form having a property failing to comply with the predefined criterion.

11. The method according to claim 1, wherein an ending point of the coating process forming the coating of the solid dosage form is controlled in accordance with the monitored property of the coating.

12. The method according to claim 1, wherein a starting point of the monitoring of the property of the coating is controlled in accordance with a characteristic of the coating process forming the coating.

13. The method according to claim 1, wherein the method further comprises adapting the monitoring of the property of the coating of the solid dosage form in accordance with a characteristic of the coating process forming the coating.

14. The method according to claim 1, wherein the monitoring of the property of the coating is performed during the presence of the solid dosage form within a coating apparatus within which a precursor of the coating is present.

15. A device for coating an at least partially solid dosage form and monitoring a property of the coating of the solid dosage form during a coating process forming the coating of the solid dosage form, the device comprising:
    a coating apparatus configured for forming the coating on the solid dosage form,
    a monitoring apparatus configured for monitoring the property of the coating of the solid dosage form in process,
    wherein at least a part of the monitoring apparatus is located so as to have insight in an interior of the coating apparatus, the interior accommodating the solid dosage form to be coated and a precursor for forming the coating, the solid dosage form being moved during the coating process into a field of view of the monitoring apparatus, and
    wherein the monitoring apparatus is configured for monitoring the property of the coating of the solid dosage form during a coating process forming the coating using low coherence interferometry.

16. The device according to claim 15, wherein the property of the coating is monitored in a time resolved manner.

17. The device according to claim 15, comprising one of the following features:
    the monitoring apparatus is configured for monitoring the property of the coating in one, two, or three spatial dimensions;
    the low coherence interferometry uses light having a central wavelength which lies between 400 nm and 8000 nm;
    the low coherence interferometry is one of the group consisting of a white light interferometry, and an optical coherence tomography;
    the monitoring apparatus is configured for monitoring the property of the coating by analyzing an obtained interference pattern of the low coherence interferometry;
    the property of the coating is one of the group consisting of a thickness of the coating, a homogeneity of the coating, a thickness variation of the coating or a quality of an attachment of the coating to the solid dosage form;
    the device further comprises a quality determining unit configured for determining information indicative of a quality of a coating of a solid dosage form by comparing the monitored property of the coating with a predefined criterion;
    the device further comprises a post-processing unit configured for post-processing the solid dosage form having a property failing to comply with the predefined criterion;
    at least a part of the monitoring apparatus is located within the coating apparatus, wherein the part of the monitoring apparatus is located particularly in a mantle of the coating apparatus;
    the coating apparatus comprises at least one of the group consisting of a rotating drum coating system, a tumble coating system, and a fluid bed coating system;

the monitoring apparatus is further configured for starting the monitoring of the property of the coating in accordance with a characteristic of the coating apparatus.

18. The device according to claim 15, wherein the monitoring apparatus is further configured for generating a signal indicating the property of the coating, and wherein the coating apparatus is further configured for ending the coating process forming the coating of the solid dosage form based on the signal.

19. The device according to claim 15, wherein the monitoring apparatus is further configured for adapting the monitoring of the property of the coating of the solid dosage form based on a characteristic of the coating apparatus.

20. The device according to claim 15, wherein the monitoring apparatus and the coating apparatus are arranged relatively to one another and are configured so that the solid dosage form is moved during the coating process within the coating apparatus and thereby moves into a field of view of the monitoring apparatus, whereby the monitoring apparatus is enabled to perform the low coherence interferometry on the solid dosage form while remaining within the field of view.

* * * * *